US 10,524,498 B2

(12) United States Patent
White et al.

(10) Patent No.: US 10,524,498 B2
(45) Date of Patent: Jan. 7, 2020

(54) APPARATUS FOR DETECTING A SUBSTANCE IN A ROD SHAPED ARTICLE OF THE TOBACCO INDUSTRY

(71) Applicant: British American Tobacco (Investments) Limited, London (GB)

(72) Inventors: Julian Dennis White, Cambridge (GB); Martin John Horrod, Cambridge (GB); Andrew Jonathan Bray, London (GB); Gary Fallon, London (GB)

(73) Assignee: BRITISH AMERICAN TOBACCO (INVESTMENTS) LIMITED, London (GB)

( * ) Notice: Subject to any disclaimer, the term of this patent is extended or adjusted under 35 U.S.C. 154(b) by 723 days.

(21) Appl. No.: 15/023,610

(22) PCT Filed: Aug. 28, 2014

(86) PCT No.: PCT/EP2014/068297
§ 371 (c)(1),
(2) Date: Mar. 21, 2016

(87) PCT Pub. No.: WO2015/039849
PCT Pub. Date: Mar. 26, 2015

(65) Prior Publication Data
US 2016/0205995 A1 Jul. 21, 2016

(30) Foreign Application Priority Data
Sep. 20, 2013 (GB) .................................. 1316689.7

(51) Int. Cl.
*A24C 5/34* (2006.01)
*A24D 3/02* (2006.01)
*G01N 21/3577* (2014.01)

(52) U.S. Cl.
CPC ............ *A24C 5/3412* (2013.01); *A24D 3/025* (2013.01); *G01N 21/3577* (2013.01); *G01N 2201/0612* (2013.01); *G01N 2201/08* (2013.01)

(58) Field of Classification Search
CPC ...... A24C 5/3412; A24D 3/025; G01N 23/06; G01N 21/3577; G01N 2201/0612; G01N 21/3554; G01N 21/3151
(Continued)

(56) References Cited

U.S. PATENT DOCUMENTS 3,270,200 A * 8/1966 Rhodes .................. G01N 23/06
378/45
3,588,601 A * 6/1971 Yamasaki ................. G01J 3/10
313/572
(Continued)

FOREIGN PATENT DOCUMENTS

CN  1285636 A  2/2001
EP  0906729 A2  4/1999
(Continued)

OTHER PUBLICATIONS

International Preliminary Report on Patentability for corresponding application PCT/EP2014/068297 filed Aug. 28, 2014; dated Oct. 29, 2015.
(Continued)

*Primary Examiner* — Alexander M Valvis
*Assistant Examiner* — Katie L Gerth
(74) *Attorney, Agent, or Firm* — Cantor Colburn LLP

(57) ABSTRACT

An apparatus (1) for detecting a substance in a rod shaped article of the tobacco industry (2), the apparatus (1) including one or more sources (10,11) of electromagnetic radiation, one or more detectors (26, 27) and a processor (32). The one or more sources (10, 11) are configured to generate
(Continued)

electromagnetic radiation at first and second wavelengths ($\lambda 1$, $\lambda 2$). The one or more detectors (26, 27) are configured to detect the first and second wavelengths ($\lambda 1$, $\lambda 2$) after propagation in the rod shaped article (2), lo and to generate signals (A, B) based on the amount of radiation received at each wavelength ($\lambda 1$, $\lambda 2$). The processor (32) is configured to process the signals (A, B) to determine information relating to the presence of the substance, based on the relative amount of radiation received at the first and second wavelengths.

17 Claims, 4 Drawing Sheets

(58) Field of Classification Search
USPC .............................................. 131/905; 493/4
See application file for complete search history.

(56) References Cited

U.S. PATENT DOCUMENTS

| | | | | |
|---|---|---|---|---|
| 3,986,776 | A * | 10/1976 | George | G01J 3/42 356/319 |
| 4,644,176 | A * | 2/1987 | Heitmann | G01N 21/952 131/281 |
| 4,707,652 | A * | 11/1987 | Lowitz | G01N 22/00 250/225 |
| 4,795,256 | A * | 1/1989 | Krause | G01J 3/427 356/318 |
| 4,851,817 | A | 7/1989 | Brossia | |
| 4,942,363 | A * | 7/1990 | Lowitz | A24C 5/3412 131/905 |
| 5,086,279 | A | 2/1992 | Wochnowski | |
| 5,568,818 | A * | 10/1996 | Neri | A24C 5/3412 131/84.4 |
| 6,104,946 | A * | 8/2000 | Tsuchiya | A61B 5/0091 356/432 |
| 6,614,531 | B2 * | 9/2003 | Sato | A24B 1/04 356/237.1 |
| 2001/0046047 | A1 * | 11/2001 | Ryer | G01J 3/02 356/328 |
| 2002/0030820 | A1 | 3/2002 | Kida | |
| 2002/0039185 | A1 * | 4/2002 | Sato | A24B 1/04 356/429 |
| 2004/0118416 | A1 * | 6/2004 | Seymour | A24C 5/00 131/60 |
| 2004/0118419 | A1 * | 6/2004 | Hancock | A24C 5/00 131/280 |
| 2007/0024852 | A1 * | 2/2007 | White | G01N 21/645 356/417 |
| 2007/0091326 | A1 * | 4/2007 | Schroeder | A24C 5/3412 356/625 |
| 2007/0291898 | A1 * | 12/2007 | Groves | A61B 6/4241 378/51 |
| 2009/0194118 | A1 | 8/2009 | Ademe | |
| 2009/0250595 | A1 * | 10/2009 | Kalitsis | G01N 21/3563 250/208.2 |
| 2010/0051905 | A1 * | 3/2010 | Iguchi | B82Y 20/00 257/14 |
| 2011/0217058 | A1 | 9/2011 | Honda | |
| 2012/0154498 | A1 | 6/2012 | Chiwata | |
| 2013/0028615 | A1 | 1/2013 | Satoh | |
| 2013/0057861 | A1 | 3/2013 | Ishii | |

FOREIGN PATENT DOCUMENTS

| | | |
|---|---|---|
| EP | 1702524 A1 | 9/2006 |
| EP | 2243385 A2 | 10/2010 |
| JP | 2001228727 A | 8/2001 |
| JP | 2010197535 A | 9/2010 |
| JP | 2011226801 A | 11/2011 |
| WO | 9709606 A1 | 3/1997 |
| WO | 2005047872 A1 | 5/2005 |
| WO | 2006092962 A1 | 9/2006 |
| WO | 2013005641 A1 | 1/2013 |

OTHER PUBLICATIONS

International Search Report for corresponding application PCT/EP2014/068297 filed Aug. 28, 2014; dated Feb. 11, 2015.
Written Opinion for corresponding application PCT/EP2014/068297 filed Aug. 28, 2014; dated Feb. 11, 2015.

* cited by examiner

APPARATUS FOR DETECTING A SUBSTANCE IN A ROD SHAPED ARTICLE OF THE TOBACCO INDUSTRY

TECHNICAL FIELD

The specification relates to apparatus for detecting a substance, such as water, in a rod shaped article of the tobacco industry, for example a filter rod.

BACKGROUND

Filter rods used in the manufacture of filtered cigarettes conventionally comprise a plug of cellulose acetate tow wrapped with a paper plugwrap. Known filter rod making machines comprise a garniture which receives a flow of tow and a ribbon of filter paper and forms a paper wrapped elongate filter rod, which is subsequently cut into filter rod segments.

SUMMARY

In an embodiment there is provided an apparatus for detecting a substance in a rod shaped article of the tobacco industry, comprising: one or more sources of electromagnetic radiation, configured to generate electromagnetic radiation at first and second wavelengths; one or more detectors, configured to detect the first and second wavelengths after propagation in the rod shaped article, wherein the one or more detectors are configured to generate signals based on the amount of radiation received at each wavelength; and a processor configured to process the signals to determine information relating to the presence of the substance, based on the relative amount of radiation received at the first and second wavelengths.

The apparatus may comprise an optical output configured to output the first and second wavelengths co-linearly, and to direct the combined radiation towards said rod shaped article. Moreover, the apparatus may comprise an optical combiner for combining the first and second wavelengths and providing the combined radiation to the optical output.

The one or more detectors may comprise a first detector configured to detect radiation at the first wavelength and a second detector configured detect radiation at the second wavelength; and the apparatus may comprise an optical separator for separating the first and second wavelengths after propagation in the rod shaped article in order to provide radiation received at the first wavelength to the first detector and radiation received at the second wavelength to the second detector.

The apparatus may be an apparatus for detecting a capsule in a rod shaped article of the tobacco industry by detecting the substance.

The one or more detectors may be configured to detect the first and second wavelengths after transmittance through the rod shaped article.

The apparatus may comprise an inspection area for the rod shaped article to be passed through and may be configured such that the first and second wavelengths propagate through a region of the rod shaped article as the rod shaped article is passed through the inspection area.

In another embodiment there is provided a tobacco industry apparatus for manufacturing a rod shaped article, comprising the apparatus for detecting a substance in a tobacco industry rod article of the above embodiment. For example, the tobacco industry apparatus for manufacturing a rod shaped article may comprises a filter maker, a tobacco rod maker or a cigarette assembler.

The substance detected by the apparatus may comprise a liquid substance. The substance may comprise a chemical, for example water, menthol, Triacetin, glycol, glycerol and/or a chemical constituent of palm oil.

As used herein, the term "rod shaped article of the tobacco industry" includes solid rod or tubular articles of the tobacco industry, such as filters or tobacco rods. Furthermore, the term includes rod or tube shaped assembled smokeable products such as cigarettes, cigars and cigarillos, whether based on tobacco, tobacco derivatives, expanded tobacco, reconstituted tobacco or tobacco substitutes, and also heat-not-burn products (i.e. products in which flavour is generated from a smoking material by the application of heat without causing combustion of the material). Any reference to a filter, tobacco rod or an assembled smokable product such as a cigarette can be replaced by a reference to a rod shaped article of the tobacco industry.

BRIEF DESCRIPTION OF THE DRAWINGS

Embodiments will now be described, by way of example only, with reference to the accompanying drawings, in which.

DETAILED DESCRIPTION

Figure 1:
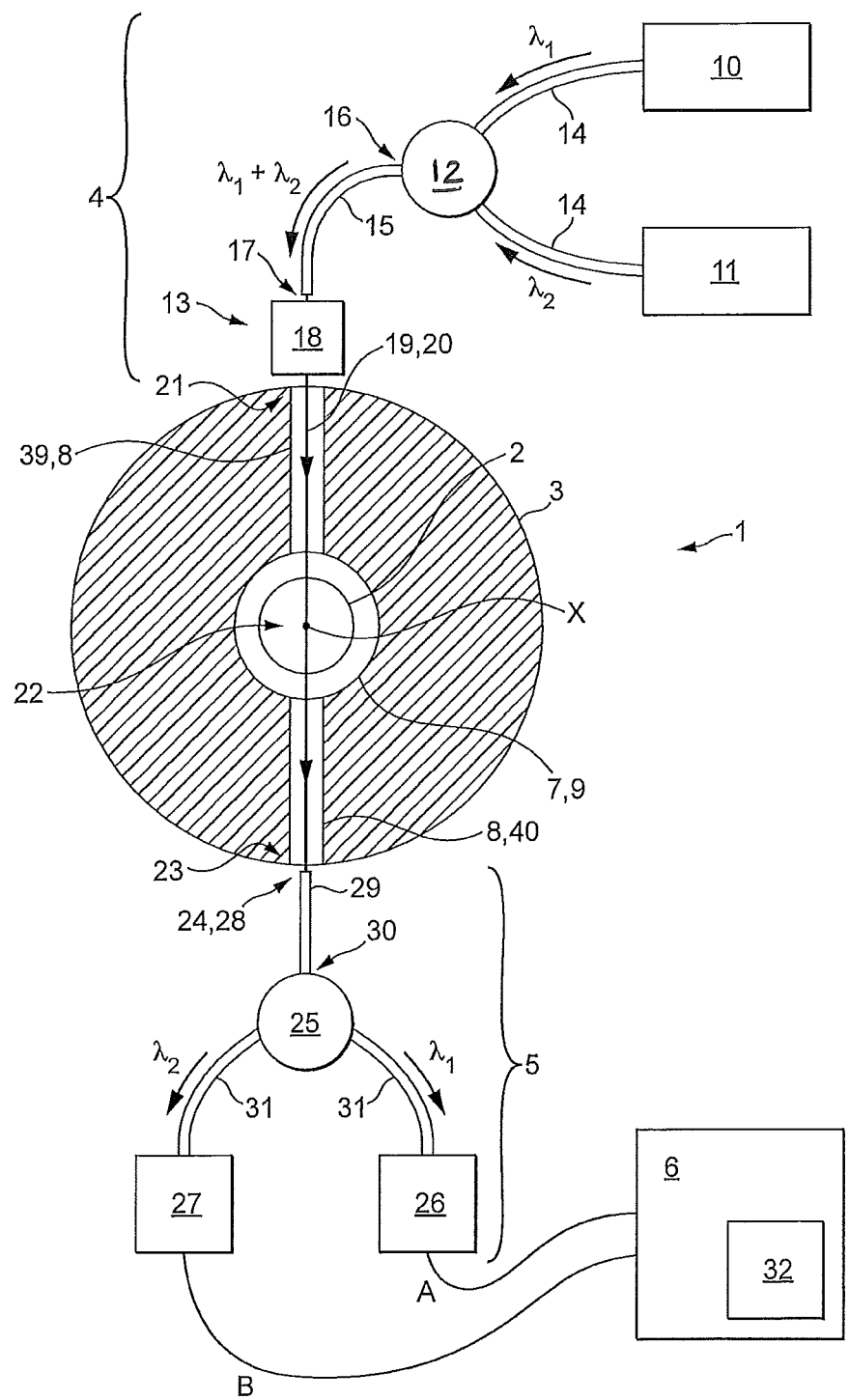
FIG. 1 is a schematic view of an apparatus for detecting water in filter rods.

FIG. 1 is a schematic view of an apparatus 1 for detecting water in filter rods 2. The apparatus 1 comprises an inspection block 3, an optical output arrangement 4, a detection arrangement 5 and a processing device 6. The inspection block 3 is configured to receive a filter 2 for inspection. The optical output arrangement 4 is configured to output electromagnetic radiation at a first wavelength $\lambda 1$ and a second wavelength $\lambda 2$ towards the received filter 2. The first and second wavelengths $\lambda 1$, $\lambda 2$ are different and attenuate by different amounts when passed through water. The detection arrangement 5 is configured to detect the intensity of the first and second wavelengths $\lambda 1$, $\lambda 2$ after they have propagated through the filter rod 2 and to transmit signals A, B containing this information to the processing device 6. The processing device 6 is configured to determine information relating to the presence of water within the filter rod 2, based on the relative intensity of the radiation received at the first wavelength $\lambda 1$ and the second wavelength $\lambda 2$.

Due to ambient air humidity, a manufactured filter rod 2 may include a very small amount of water dispersed throughout its structure. The information relating to the presence of water includes information relating to the amount of water within inspected filter rods 2. For example, the apparatus 1 may identify manufacturing errors by detecting filters 2 which include an incorrect amount of water or an incorrect distribution of water along their length.

Figure 2:
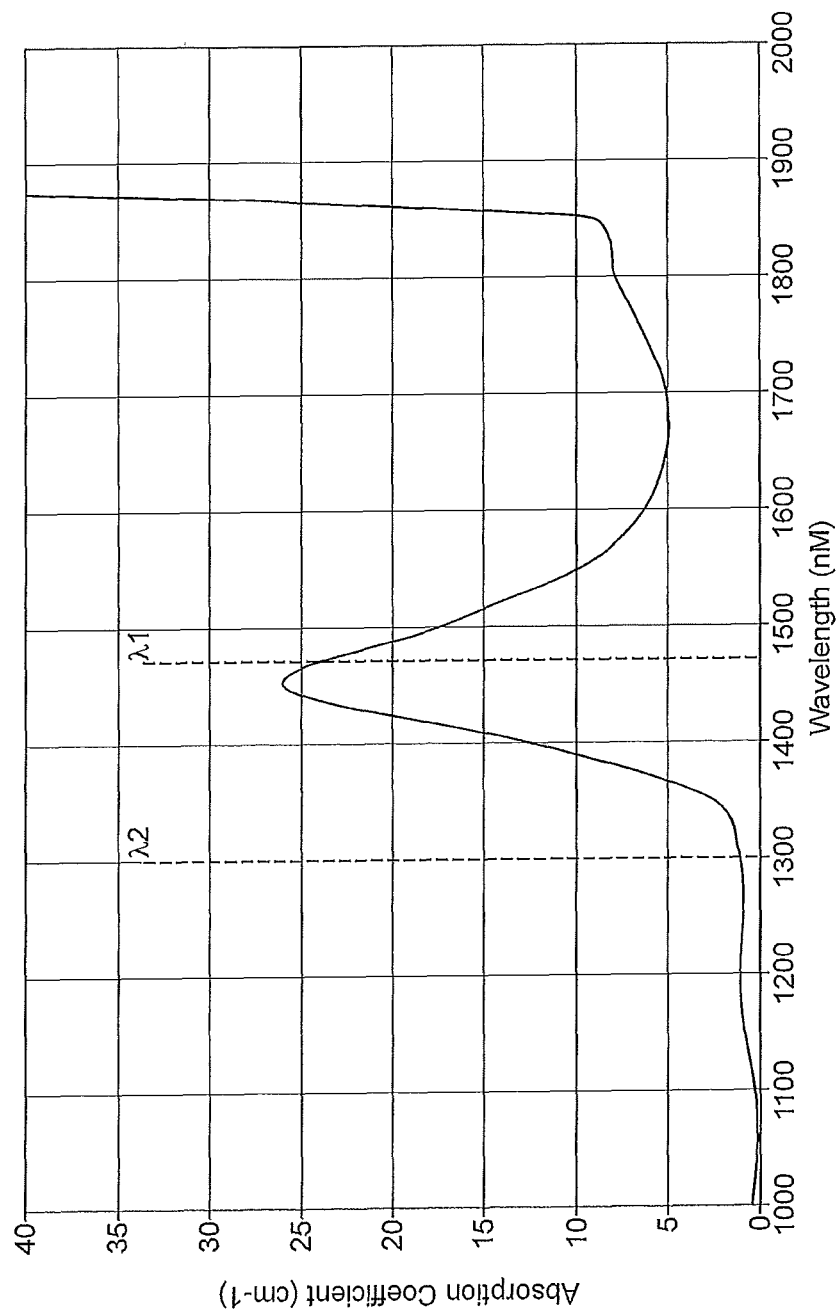
FIG. 2 is a graph illustrating part of the absorption spectrum of water.

FIG. 2 is a graph illustrating part of the absorption spectrum of water, which includes an absorption peak centred around 1450 nm. The first and second wavelengths $\lambda 1$, $\lambda 2$ are also indicated in FIG. 1. The first wavelength $\lambda 1$ is at approximately 1470 nm and the second wavelength $\lambda 2$ is at approximately 1310 nm. As can be seen from FIG. 1, the location in the spectrum of the first and second wavelengths $\lambda 1$, $\lambda 2$ relative to the absorption peak means that the absorption coefficient of water is approximately 16 times greater at the first wavelength $\lambda 1$ than at the second wavelength $\lambda 2$.

The inspection block 3 comprises an inspection hole 7 and a radiation passageway 8. One end of the inspection hole 7 comprises a rod input 9, configured to receive a filter 2 such that the filter is coaxial with the inspection hole 7 and can pass coaxially through the inspection hole 7 for inspection. The radiation passageway 8 is a hole through the inspection block 3 intersecting and perpendicular to the inspection hole 7. A filter 2 is shown as having been received by the rod input 9 and as being located within the inspection hole 7. The filter 2 includes an amount of water.

The optical output arrangement 4 comprises a first source 10 of radiation for generating radiation at the first wavelength $\lambda 1$, a second source 11 of radiation for generating radiation at the second wavelength $\lambda 2$, an optical combiner 12 and an optical output 13. For example, the first and second sources 10, 11 may be laser diodes with output powers of 1 to 2 Watts. The first and second sources 10, 11 are connected to the optical combiner 12 via optical fibres 14, such that the generated first and second wavelengths $\lambda 1$, $\lambda 2$ are provided to the optical combiner 12 via the optical fibres 14. Optical coupling between laser diodes and optical fibres is well known per se and will not be described here. The optical combiner 12 is connected to a further, single optical fibre 15 and is configured to couple the generated first and second wavelengths $\lambda 1$, $\lambda 2$ into a first end 16 of the single optical fibre 15. For example, the optical combiner 12 may be a wavelength division multiplexer (WDM). The optical output 13 comprises the second end 17 of the optical fibre 15 and an optical collimator 18. The second end 17 of the optical fibre 15 outputs the combined first and second wavelengths $\lambda 1$, $\lambda 2$ into the air towards the optical collimator 18, and the optical collimator 18 forms the combined first and second wavelengths $\lambda 1$, $\lambda 2$ into two co-linear beams 19, 20. The optical output 13 is mounted at a first end 21 of the radiation passageway 8 and is configured such that the two co-linear beams 19, 20 pass coaxially into the radiation passageway 8 and thereby encounter a region 22 of the filter 2. Radiation of the co-linear beams 19, 20 which passes through the region 22 of the filter 2 continues along the radiation passageway 8 towards its second end 23.

As the output first and second wavelengths $\lambda 1$, $\lambda 2$ pass through the region 22 of the filter 2, they are attenuated by the structure of the filter 2 and by water present in the region of the filter. As the first and second wavelengths $\lambda 1$, $\lambda 2$ are similar, the attenuation of each due to the structural elements of the filter 2, such as cellulose fibres and mineral fillers of the filter, will be similar. However, due to the location of the wavelengths $\lambda 1$, $\lambda 2$ in the optical absorption spectrum of water, the attenuation by water of the first wavelength $\lambda 1$ is significantly greater than that of the second wavelength $\lambda 2$. The difference in the intensity of the first and second wavelengths $\lambda 1$, $\lambda 2$ emerging from the region 22 of the filter 2 is therefore indicative of the amount of water in the region 22 of the filter 2.

The detector arrangement 5 comprises an optical input 24, an optical separator 25, a first detector 26 and a second detector 27. The optical input 24 comprises a first end 28 of an optical fibre 29, the second end 30 of which is connected to the optical separator 25. The first end 28 is located at the second end 23 of the radiation passageway 8, facing the optical output 13, and is configured such that first and second wavelengths $\lambda 1$, $\lambda 2$ reaching the second end 23 of the passageway 8 enter the first end 28 of the optical fibre 29. First and second wavelengths $\lambda 1$, $\lambda 2$ received at the optical input 24 pass along the optical fibre 29 to the optical separator 25. The optical separator 25 is connected to the first and second detectors 26, 27 by respective optical fibres 31 and is configured to separate the received first and second wavelengths $\lambda 1$, $\lambda 2$ so as to provide the first wavelength $\lambda 1$ to the first detector 26 and the second wavelength $\lambda 2$ to the second detector 27. For example, the optical separator 25 may be a WDM. Each of the first and second detectors 26, 27 is configured to transmit electrical signals A, B to the processing device 6 based on the intensity of radiation they receive.

The processing device 6 comprises a processor 32 configured to process the signals A, B from the first and second detectors 26, 27 in order to determine the information relating to the presence of water within the region 22 of the filter 2, based on the relative intensity of the first and second wavelengths $\lambda 1$, $\lambda 2$ after their passage through the region 22 of the filter 2. The information relating to the presence of water within the region 22 of the filter 2 includes information relating to the amount of water within the region 22 of the filter 2. For example, the processor 32 may determine an amount by which the intensity of the received first wavelength $\lambda 1$ is less than that of the received second wavelength $\lambda 2$ and may use this to approximate the amount of water present in the region 22 of the filter rod 2.

As will now be described with reference to FIG. 3, the apparatus 1 receives a batch 33 of filters 2, each filter 2 of the batch being conveyed in turn through the inspection block 3 for inspection. Moreover, the processor 32 is configured to sample the signals A, B from the detectors 26, 27 at regular intervals during the conveyance of each filter 2 through the inspection block 3 so as to determine the information relating to the presence of water within each filter 2 at a plurality of regions along its length.

Figure 3:
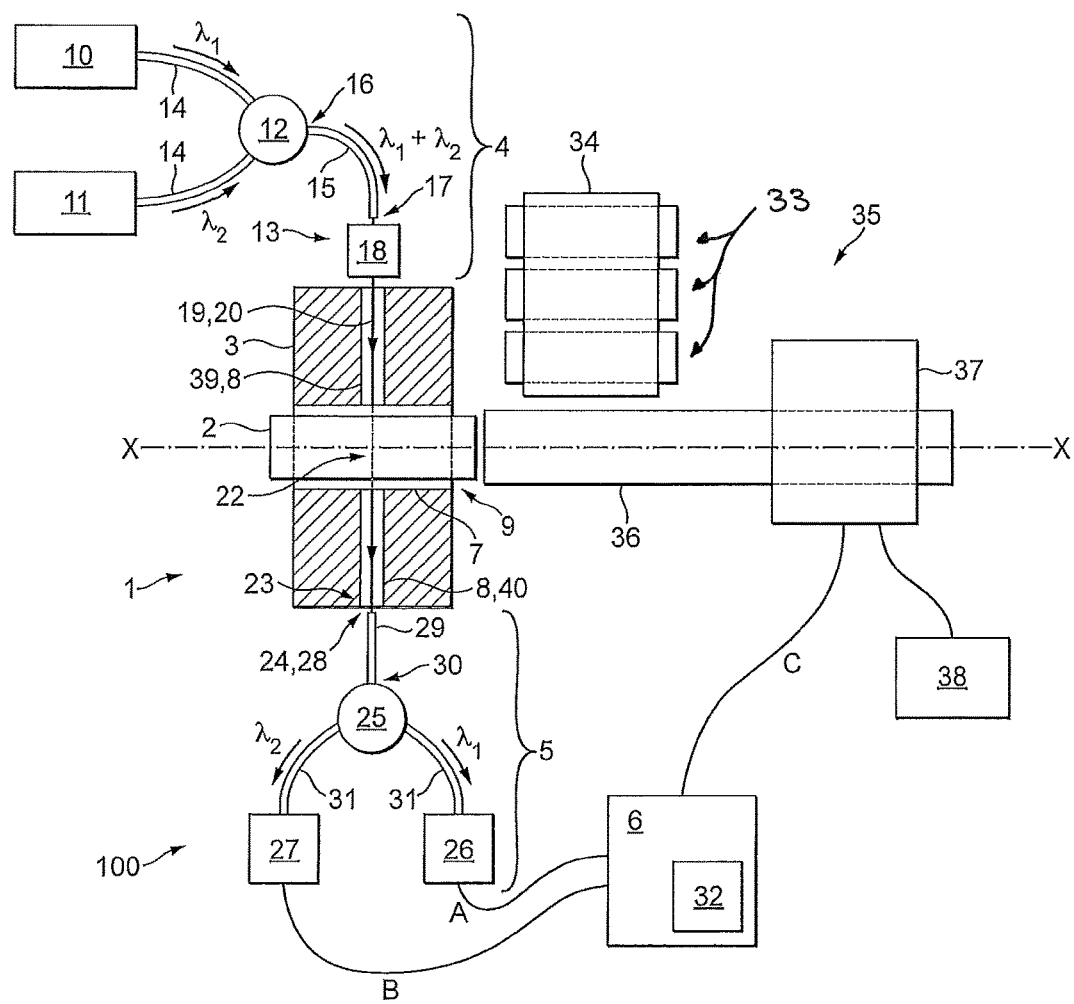
FIG. 3 shows a side view of an apparatus incorporating the apparatus for detecting water of FIG. 1.

FIG. 3 shows a side view of an "offline" apparatus 100 incorporating the water detecting apparatus 1. As can be seen in FIG. 3, the apparatus 100 has a hopper 34, configured to receive a batch 33 of filters 2, and a conveyer arrangement 35. The conveyer arrangement 35 is configured to receive filters 2 successively from the hopper 34 and to convey each received filter 2 to and coaxially through the rod input 9. The conveyer arrangement 35 comprises a pusher rod 36, a motor 37 and a motor controller 38. The motor 37 is configured to move the pusher rod 36 and to output information C on the position of the pusher rod 36 to the processing device 6. For example, the motor 37 may comprise a rotary encoder. The motor controller 38 is configured to interface with and control the motor 37. In embodiments, the motor controller 38 is controlled by the processing device 6.

In operation, a filter 2 is received by the conveyer arrangement 35 from the hopper 34. The pusher rod 36 then pushes the received filter 2 through the inspection hole 7 and therein through the output first and second wavelengths $\lambda 1$, $\lambda 2$. The processor 32 samples the signals A, B from the detectors 26, 27 at regular intervals during the filter's 2 conveyance. Each sample corresponds to a different region 22 of the filter 2 along the filter's length. The processor 32 may be further configured to use the information C on the position of the pusher rod 36 during the conveyance of the filter 2 to determine the location of each inspected region 22 of the filter 2 along its length. This process is then repeated until all of the filters 2 of the batch 33 of filters have been inspected.

Many alternatives and variations of the embodiments described herein are possible. Example alternatives and variations are as follows.

Although FIG. 3 shows an "offline" device 100 having a hopper 34 to receive filter rods 2 to be inspected, alternatively the apparatus 1 could be implemented in an online device as part of a filter rod making machine. For example, in one embodiment a filter rod making machine is provided comprising the apparatus 1, wherein the inspection block 3 is positioned in the path of the elongate filter rod formed in the rod making machine so that the elongate rod passes through the inspection hole 7 so as to be analysed by the apparatus 1.

The apparatus 1 is described above as being configured to detect water in filter rods 2. However, the apparatus 1 may additionally or alternatively be configured to detect one or more other chemicals. For example, the apparatus 1 may be configured to detect menthol, Triacetin, glycol, glycerol and/or a chemical constituent of palm oil. Moreover, the information relating to the presence of the one or more chemicals may indicate only whether the one or more chemicals are present or not in an inspected rod article.

Figure 4:
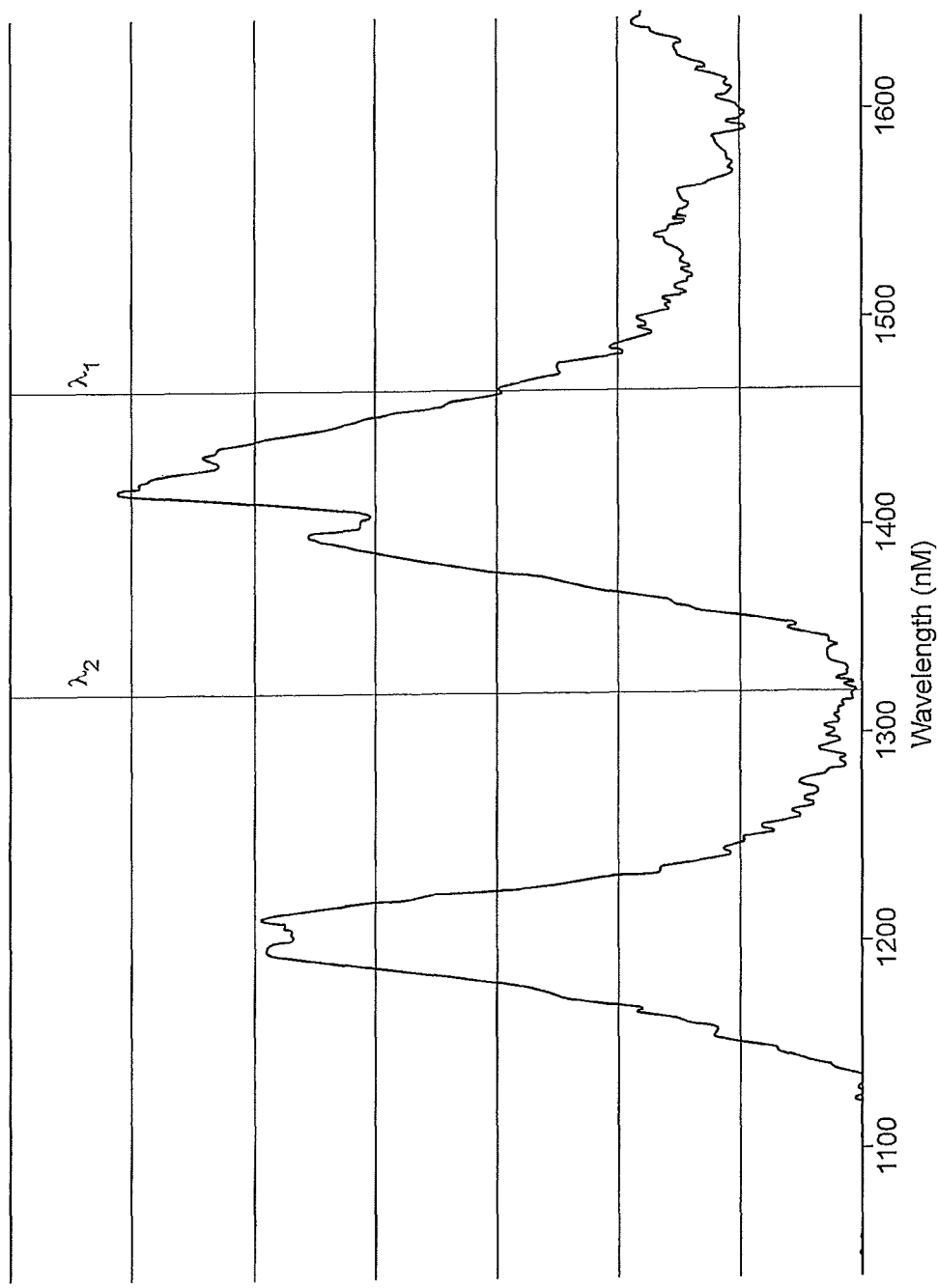
FIG. 4 illustrates part of the absorption spectrum of menthol.

With reference to the detection of menthol, FIG. 4 illustrates part of the absorption spectrum of menthol, having two significant absorption peaks centred approximately at 1200 nm and 4150 nm respectively. Moreover, FIG. 4 shows example locations of the first and second wavelengths $\lambda1$, $\lambda2$. The first wavelength $\lambda1$ is at approximately 1470 nm and the second wavelength $\lambda2$ is at approximately 1310 nm. As can be seen from FIG. 4, the location in the spectrum of the first and second wavelengths $\lambda1$, $\lambda2$ relative to the absorption peaks is such that the absorption coefficient of menthol is approximately 15 times greater at the first wavelength $\lambda1$ than at the second wavelength $\lambda2$.

The apparatus 1 is described above as being configured to detect one or more chemicals in filter rods 2. However, the apparatus 1 may be configured to detect objects within filter rods 2 by detecting one or more chemicals in or on the objects. For example, the apparatus 1 may be configured to detect capsules within filter rods 2 wherein the capsules contain a chemical.

The apparatus 1 is described above as being configured to detect one or more chemicals, based on an effect of the one or more chemicals on the first and second wavelengths. The effect is described above as a differing amount of attenuation, through absorption, between the first and second wavelengths. However, it should be noted that the apparatus 1 may be configured to detect the one or more chemicals, based on other frequency-dependent effects of the one or more chemicals on the first and second wavelengths. For example the aforementioned attenuation may be due scattering, in addition to or instead of absorption.

The apparatus 1 is described above as being configured to detect one or more chemicals or objects within filter rods 1. However, the apparatus 1 may be configured to detect one or more chemicals or objects within other rod shaped articles of the tobacco industry, such as tobacco rods or assembled cigarettes.

The detection arrangement 5 is described above as being configured to detect the intensity of the first and second wavelengths $\lambda1$, $\lambda2$ after they have propagated through the filter rod 2. However, the apparatus 1 may be configured such that the aforementioned propagation of the first and second wavelengths $\lambda1$, $\lambda2$ through the filter 2 involves the first and second wavelengths $\lambda1$, $\lambda2$ being redirected by a region 22 of the filter 2. For example, a first portion 39 of the radiation passageway 8 between its first end 21 and its intersection with the inspection hole 7 may not be aligned with the remaining second portion 40 of the radiation passageway 8, between its second end 23 and its intersection with the inspection hole 7. Moreover, radiation of the first and second wavelengths $\lambda1$, $\lambda2$ may be scattered, and thereby redirected, by a region 22 of the filter 2 and a portion of this scattered radiation may enter the second portion 40 of the radiation passageway 8. As the optical input 24 of the detector arrangement 5 is located at the second end 23 of the radiation passageway 8, in this case the detection arrangement 5 detects the intensity of the first and second wavelengths $\lambda1$, $\lambda2$ after they have been redirected by a region 22 of the filter rod 2.

The apparatus 1 is described above as being configured to output the first and second wavelengths $\lambda1$, $\lambda2$ as two co-linear beams 19, 20. However, the apparatus 1 may be configured such that the first and second wavelengths $\lambda1$, $\lambda2$ are output as two beams which do not overlap, do not substantially overlap or which intersect over a limited area only. For example, the inspection block 3 may comprise a second radiation passageway, separate from the first radiation passageway, and the first and second wavelengths $\lambda1$, $\lambda2$ may be passed through the first and second radiation passageways respectively. For instance, instead of employing an optical combiner 12, the optical output arrangement 4 may be configured such that the first source 10 is connected via an optical fibre directly to the first radiation passageway 8, and such that the second source 11 is directly connected via a further optical fibre to the second radiation passageway. Moreover, instead of an optical splitter 25, the detection arrangement 5 may be configured such that first detector 26 is connected via an optical fibre directly to the first radiation passageway 8 and such that the second detector 27 is connected via a further optical fibre directly to the second radiation passageway. The first and second radiation passageways may for example be separated in a direction parallel to the axis X of the inspection hole 7. Alternatively or additionally, the first and second radiation passageways may be separated by virtue of their intersecting the inspection hole 7 at different angles.

In order to address various issues and advance the art, the entirety of this disclosure shows by way of illustration various embodiments in which the claimed invention(s) may be practiced and provide for superior inspection of rod shaped articles of the tobacco industry. The advantages and features of the disclosure are of a representative sample of embodiments only, and are not exhaustive and/or exclusive. They are presented only to assist in understanding and teach the claimed features. It is to be understood that advantages, embodiments, examples, functions, features, structures, and/or other aspects of the disclosure are not to be considered limitations on the disclosure as defined by the claims or limitations on equivalents to the claims, and that other embodiments may be utilised and modifications may be made without departing from the scope and/or spirit of the disclosure. Various embodiments may suitably comprise, consist of, or consist essentially of, various combinations of the disclosed elements, components, features, parts, steps, means, etc. In addition, the disclosure includes other inventions not presently claimed, but which may be claimed in future. Any feature of any embodiment can be used independently of, or in combination with, any other feature.

The invention claimed is:

1. Apparatus for detecting a substance in a rod shaped article of the tobacco industry, comprising:
   one or more sources of electromagnetic radiation, configured to generate electromagnetic radiation at first and second wavelengths, said first and second wavelengths being different from each other, said one or more sources of electromagnetic radiation being configured to generate the first wavelength at a peak in the optical absorption spectrum of the substance;

one or more detectors, configured to detect the first and second wavelengths after propagation through the rod shaped article, wherein the one or more detectors are configured to generate signals based on the amount of radiation received at each wavelength; and a processor configured to process the signals to determine information relating to the presence of the substance, based on the relative amount of radiation received at the first and second wavelengths.

2. The apparatus of claim 1, comprising an optical output configured to output the first and second wavelengths co-linearly, and direct them towards said rod shaped article.

3. The apparatus of claim 2, comprising an optical combiner for combining the first and second wavelengths and providing the combined radiation to the optical output.

4. The apparatus of claim 3, wherein the optical combiner is a wavelength division multiplexer.

5. The apparatus of claim 1, wherein the one or more detectors comprise a first detector configured to detect radiation at the first wavelength and a second detector configured to detect radiation at the second wavelength; and the apparatus comprises an optical separator for separating the first and second wavelengths after propagation in the rod shaped article in order to provide radiation received at the first wavelength to the first detector and radiation received at the second wavelength to the second detector.

6. The apparatus of claim 5, wherein the optical splitter comprises a wavelength division multiplexer.

7. The apparatus of claim 1, wherein the substance is menthol or water.

8. The apparatus of claim 1, wherein the apparatus is an apparatus for detecting a capsule in a rod shaped article of the tobacco industry by detecting a substance within the capsule.

9. The apparatus of claim 1, wherein the first wavelength is approximately 1.47 μm.

10. The apparatus of claim 1, wherein the second wavelength is approximately 1.31 μm.

11. The apparatus of claim 1, wherein the one or more detectors are configured to detect the first and second wavelengths after transmittance through the rod shaped article.

12. The apparatus of claim 1, wherein the information relating to the presence of the substance includes information on an amount of the substance present in the rod shaped article.

13. The apparatus of claim 1, further comprising an inspection area for the rod shaped article to be passed through, and configured such that the first and second wavelengths propagate through a region of the rod shaped article as the rod shaped article is passed through the inspection area.

14. Tobacco industry apparatus for manufacturing a rod shaped article, comprising the apparatus as claimed in claim 1.

15. The tobacco industry apparatus of claim 14, comprising a filter maker.

16. The tobacco industry apparatus of claim 14, wherein the tobacco industry apparatus comprises a tobacco rod maker.

17. The tobacco industry apparatus of claim 14, wherein the tobacco industry apparatus comprises a cigarette assembler.

* * * * *